United States Patent [19]

Enevold

[11] Patent Number: 6,020,200
[45] Date of Patent: Feb. 1, 2000

[54] ENCAPSULATION COMPOSITIONS AND METHODS

[75] Inventor: Karl C. Enevold, Newark, Calif.

[73] Assignee: Metabolex, Inc., Hayward, Calif.

[21] Appl. No.: 08/609,164

[22] Filed: Mar. 1, 1996

Related U.S. Application Data

[63] Continuation-in-part of application No. 08/399,295, Mar. 3, 1995.

[51] Int. Cl.$^7$ .............................. C12N 5/00; C12N 5/06
[52] U.S. Cl. .......................... 435/382; 264/4.3; 264/4.32; 424/425; 424/484; 424/491; 428/402.2; 428/402.24; 435/177; 435/178; 514/866; 530/356
[58] Field of Search .................................. 435/177, 178, 435/382; 424/491, 425; 514/866; 530/356

[56] References Cited

U.S. PATENT DOCUMENTS

| | | | |
|---|---|---|---|
| 3,972,776 | 8/1976 | Vieth et al. | 435/177 |
| 4,164,559 | 8/1979 | Miyata et al. | 424/428 |
| 4,177,038 | 12/1979 | Biebricher et al. | 8/192 |
| 4,352,883 | 10/1982 | Lim | 435/178 |
| 4,391,909 | 7/1983 | Lim | 435/178 |
| 4,407,957 | 10/1983 | Lim | 435/178 |
| 4,409,331 | 10/1983 | Lim | 435/178 |
| 4,543,332 | 9/1985 | Jao et al. | 435/180 |
| 4,592,098 | 6/1986 | Magnes | 4/508 |
| 4,647,536 | 3/1987 | Mosbach et al. | 435/177 |
| 4,663,286 | 5/1987 | Tsang et al. | 435/178 |
| 4,673,566 | 6/1987 | Goosen et al. | 424/424 |
| 4,689,293 | 8/1987 | Goosen et al. | 435/1 |
| 4,696,286 | 9/1987 | Cochrum | 128/1 |
| 4,744,933 | 5/1988 | Rha et al. | 264/4.3 |
| 4,749,620 | 6/1988 | Rha et al. | 428/402.2 |
| 4,789,550 | 12/1988 | Hommel et al. | 424/493 |
| 4,791,061 | 12/1988 | Sumino et al. | 435/178 |
| 4,798,786 | 1/1989 | Tice et al. | 435/177 |
| 4,803,168 | 2/1989 | Jarvis | 435/240.22 |
| 4,806,355 | 2/1989 | Goosen et al. | 424/424 |
| 4,824,916 | 4/1989 | Kerschner et al. | 525/420 |
| 4,902,295 | 2/1990 | Walthall et al. | 623/11 |
| 4,927,761 | 5/1990 | Reading et al. | 435/177 X |
| 4,956,128 | 9/1990 | Hommel et al. | 264/4 |
| 4,994,388 | 2/1991 | Hillegas et al. | 435/178 X |
| 5,041,292 | 8/1991 | Feijen | 424/484 |
| 5,182,111 | 1/1993 | Aebischer et al. | 435/177 X |
| 5,227,298 | 7/1993 | Weber et al. | 435/178 |
| 5,264,359 | 11/1993 | Enami et al. | 435/177 X |
| 5,286,495 | 2/1994 | Batich et al. | 424/490 |
| 5,334,640 | 8/1994 | Desai et al. | 524/56 |
| 5,362,478 | 11/1994 | Desai et al. | 424/9 |
| 5,487,895 | 1/1996 | Dapper et al. | 424/499 X |
| 5,731,417 | 3/1998 | Swiderek et al. | 530/356 |

FOREIGN PATENT DOCUMENTS

| | | | |
|---|---|---|---|
| 345 886B1 | 10/1993 | European Pat. Off. | A23L 1/05 |
| 2-001 287 | 1/1990 | Japan . | |
| 4-244 015 | 9/1992 | Japan . | |
| 2 094 833 | 9/1982 | United Kingdom . | |
| 2 237574 | 8/1991 | United Kingdom | C08J 3/215 |
| WO 91/01720 | 2/1991 | WIPO . | |
| WO 91/04318 | 4/1991 | WIPO | C12N 5/00 |
| WO 91/07951 | 6/1991 | WIPO | A61K 9/62 |
| WO 91/09119 | 6/1991 | WIPO | C12N 11/10 |
| WO 91/11205 | 8/1991 | WIPO | A61L 15/00 |
| WO 93/13755 | 7/1993 | WIPO . | |
| WO 93/24077 | 12/1993 | WIPO | A61F 2/02 |
| WO 93/24112 | 12/1993 | WIPO | A61K 9/48 |
| WO 94/12161 | 6/1994 | WIPO | A61K 9/50 |
| WO 94/15589 | 7/1994 | WIPO | A61K 9/50 |
| WO 94/18954 | 9/1994 | WIPO | A61K 9/48 |
| WO 94/23832 | 10/1994 | WIPO . | |
| WO 94/25503 | 11/1994 | WIPO | C08G 69/00 |
| WO 95/19430 | 7/1995 | WIPO | C12N 11/10 |

OTHER PUBLICATIONS

Van der Rest, M., "Collagens as Multidomain Proteins," *Biochimie*, 72, pp. 473–484 (1990).

Wallace, Donald G., "Early Assembly Pathways of Type I Collagen," *Biopolymers*, vol. 32, pp. 497–515 (1992).

Birk, David E. et al., "Collagen fibrillogenesis in vitro: interaction of types I and V collagen regulates fibril diameter," *Journal of Cell Science* 95, pp. 649–657 (1990).

Birk, David E. et al., "Collagen Fibrillogenesis in Vitro: Comparison of Types I, II, III," *Archives of Biochemistry and Biophysics*, vol. 235, No. 1, Nov. 15, pp. 178–185, (1984).

Hayashi, T. et al., "Factors Affecting the Interactions of Collagen Molecules as Observed by in Vitro Fibril Formation—I. Effects of Small Molecules, Especially Saccharides," *J. Biochem.*, 72 pp. 749–758 (1972).

Hayashi, T. et al., "Factors Affecting the Interactions of Collagen Molecules as Observed by in Vitro Fibril Formation—II. Effects of Species and Concentration of Anions," *J. Biochem.*, 74 pp. 253–262 (1973).

Hayashi, T. et al., "Factors Affecting the Interactions of Collagen Molecules as Observed by in Vitro Fibril Formation—III. Non–helical Regions of the Collagen Molecules," *J. Biochem.*, 76 pp. 177–186 (1974).

Birk, David E., "Kinetic Analysis of Collagen Fibrillogenesis: II. Corneal and Scleral Type I Collagen," *Collagen Rel. Res.* vol. 4, pp. 265–277 (1984).

(List continued on next page.)

*Primary Examiner*—Richard D. Lovering
*Attorney, Agent, or Firm*—Townsend & Townsend & Crew LLP

[57] ABSTRACT

The present invention generally relates to novel encapsulation compositions and methods. In particular, the invention relates to stabilized microcapsule compositions which comprise a layer of a crosslinked, mixed functionality, polymer matrix, and methods for their preparation. The encapsulated compositions may comprise the crosslinked polymer matrix layer as an inner layer, an outer layer, or an intermediate layer of an overall encapsulated composition. The compositions will generally also comprise a biological material, e.g., cells, proteins, and the like, encapsulated within the composition. The compositions and methods of the invention are useful in a variety of applications, including cell culturing and transplant therapy.

3 Claims, 6 Drawing Sheets

OTHER PUBLICATIONS

Snowden, John McK. et al., "The Formation and Thermal Stability of In Vitro Assembled Fibrils from Acid–Soluble and Pepsin–Treated Collagens," *Biochimica et Biophysica Acta,* 580 pp. 372–381 (1979).

Abuchowski et al., "Alteration of immunological properties of bovine serum albumin by covalent attachment of polyethylene glycol," *J. Biol. Chem.,* 252:3578–3581 (1977).

Brendel et al., "Improved functional survival of human islets of langerhans in three–dimensional matrix culture," *Cell Trans.,* 3:427–435 (1994).

Chao et al., "Entrapment of cultured pancreas islets in three–dimensional collagen matrices," *Cell Trans.,* 1:51–60 (1992).

Chiang et al., "Synthesis of ionic conducting interpenetrating polymer networks," *Polymer Communications,* Butterworth & Co., pp. 34–35 (1987).

Chaikof et al., "Surface topography of crosslinked poly(ethylene oxide) polysiloxane networks in the dry and hydrated states," *Polymer Communications,* 31:182–185 (1990).

Corkhill et al., "Synthetic hydrogels: 7. High EWC semi–interpenetrating polymer networks based on cellulose esters and N–containing hydrophilic monomers," *Polymer,* 31:1526–1537 (1990).

Goosen et al., *Fundamentals of Animal Cell Encapsulation and Immobilization,* CRC Press, Ch. 6, pp. 144–142 (1993).

Lim et al., "Microencapsulation of living cells and tissues," *J. Pharm. Sci.,* 70:351–354 (1981).

Lim et al., "Microencapsulated islets as bioartificial endocrine pancreas," *Science,* 210:908–910 (1981).

Lum et al., "Prolonged reversal of diabetic state in NOD mice by xenografts of microencapsulated rate islets," *Diabetes,* 40:1511–1516 (1993).

Ohgawara et al., "Maintenance of embedded pig pancreatic pseudo–islets in a collagen gel matrix: study of the effect of hydrocortisone, a collagenase inhibitor, and nicotinamide on collagenolysis and the morphogenesis of pancreatic islet–cells in collagen gel matrix," *In Vitro Cell Dev. Bio.,* 26:348–352 (1990).

ENCAPSULATION COMPOSITIONS AND METHODS

This application is a continuation-in-part of U.S. patent application Ser. No. 08/399,295 filed Mar. 3, 1995 which is incorporated herein by reference in its entirety for all purposes.

The present invention generally relates to novel encapsulation compositions and methods. In particular, the invention relates to stabilized microcapsule compositions which comprise a layer of a crosslinked, mixed functionality, polymer matrix, and methods for their preparation. The encapsulated compositions may comprise the crosslinked polymer matrix layer as an inner layer, an outer layer, or an intermediate layer of an overall encapsulated composition. The compositions will generally also comprise a biological material, e.g., cells, proteins, and the like, encapsulated within the composition. The compositions and methods of the invention are useful in a variety of applications, including cell culturing and transplant therapy.

BACKGROUND OF THE INVENTION

A variety of microencapsulation methods and compositions are known in the art. These compositions are primarily used in pharmaceutical formulations, for example, to mask the taste of bitter drugs, formulate prolonged dosage forms, separate incompatible materials, protect chemicals from moisture or oxidation, or modify the physical characteristics of the material for ease of handling and/or processing. Typical pharmaceutical encapsulation compositions include, e.g., gelatin, polyvinyl alcohol, ethylcellulose, cellulose acetatephthalate and styrene maleic anhydride. See Remington's Pharmaceutical Sciences, Mack Publishing Co., Easton, Pa. (1990).

Microencapsulation has also been applied in the treatment of diseases by transplant therapy. While traditional medical treatments for functional deficiencies of secretory and other biological organs have focused on replacing identified normal products of the deficient organ with natural or synthetic pharmaceutical agents, transplant therapy focuses on replacement of that function with cell or organ transplants. For example, the treatment of insulin-dependent diabetes mellitus, where the pancreatic islets of Langerhans are nonfunctional, can be carried out by replacing the normal secretion of insulin by the islets in the pancreas. Insulin may be supplied either by daily administration of synthetic or substitute animal insulin, or by transplantation of functional human or animal islets.

Attempts to transplant organ tissues into genetically dissimilar hosts without immunosuppression are generally defeated by the immune system of the host. Accordingly, attempts have been made to provide effective protective barrier coatings, e.g., by microencapsulation, to isolate the transplant tissues from the host immune system. However, these attempts generally have not proven to be medically practical due to incompatibility between the coating materials and the host system. As a result, these coated cell or tissue transplants are treated as foreign objects in the host's body and subject to immune rejection or destruction. Further, many of the encapsulation or coating processes developed previously have not yielded reproducible coatings having the desired porosity and thickness required for the transplanted tissue to have a long and effective functional life in the host.

Successful cell or tissue transplants generally require a coating that will prevent their destruction by a host's immune system, prevent fibrosis, and will be permeable to and allow a free diffusion of nutrients to the coated transplant and removal of the secretory and waste products from the coated transplant.

Viable tissue and cells have been immobilized in alginate capsules coated with polylysine. *J. Pharm. Sci.* 70:351–354 (1981). The use of these coated capsules in pancreatic islet transplantation to correct the diabetic state of diabetic animals has also been discussed. *Science* 210:908–909 (1981).

The prolonged reversal of the diabetic state of mice with xenografts of microencapsulated rat islets, using alginate-polylysine capsules has been reported. *Diabetes* 40:1511–1516 (1993). The development of transplants encapsulated in calcium alginate capsules reacted with polylysine is also described, for example, in U.S. Pat. Nos. 4,673,566, 4,689,293, 4,789,550, 4,806,355, and 4,789,550.

U.S. Pat. No. 4,744,933 describes encapsulating solutions containing biologically active materials in a membrane of inter-reacted alginate and polyamino acid.

U.S. Pat. No. 4,696,286 reports a method for coating transplants suitable for transplantation into genetically dissimilar individuals. The method involves coating the transplant with a surface conforming bonding bridge of a multifunctional material that binds chemically to a surface component of the transplant, which is enveloped in a semipermeable, biologically compatible layer of a polymer that binds chemically to the bonding bridge layer. A disadvantage of this method is that it relies upon specific interaction of the first polymer coating with acidic residues of proteins on the cell surface and thus may not provide complete coverage of tissues, particularly if other tissues are adhering to the tissue particles (e.g., acinar tissue on islets) and interfering with the desired bonding.

U.S. Pat. No. 5,227,298 describes a method for introducing a second alginate gel coating to cells already coated with polylysine alginate. Both the first and second coating of this method require stabilization by polylysine.

A downfall of many of the previously described encapsulation or coating compositions lies in their inability to provide a suitable immune barrier to prevent destruction of transplanted material. Further, many of the previously described encapsulation methods and compositions lack the structural integrity which would be desirable for encapsulation compositions in transplant methods as well as other applications. For example, alginate coatings described in the art are often either too thin, resulting in an insufficient barrier, too thick, resulting in a lack of permeability to nutrients and/or cell products required for continued functioning of the cells, or their thickness is not uniform, which results in a lack of predictability in the functioning of the encapsulated composition.

It would therefore be highly desirable to provide encapsulation compositions and methods for making them, which are capable of providing improved structural characteristics and immune protection. Such compositions and methods would find use, for example, in the production of individual transplants which can withstand mechanical, chemical or immune destruction within the host, and which would not provoke fibrogenic reactions impairing the transplant's function and which would additionally provide for free permeability of nutrients and secretory and waste products. The present invention meets these and other needs.

SUMMARY OF THE INVENTION

One aspect of the present invention provides stabilized microcapsule compositions which comprise at least one layer of a stabilized, crosslinked, mixed functionality polymer matrix having a defined matrix porosity (hereinafter referred to as "crosslinked polymer matrix"). In preferred aspects, the microcapsule compositions of the present invention comprise biological material coated with the layer of crosslinked polymer matrix. The biological material may be free, encapsulated or bound to a support. Preferred polymer matrices include those comprising collagen and derivatized alginate. The compositions may optionally comprise an additional layer of a biocompatible polymer, coating the crosslinked polymer matrix layer.

Also provided by the present invention are methods of encapsulating biological material. The methods comprise placing the biological material into a solution of a mixed functionality polymer which is capable of being crosslinked, whereby the polymer nucleates around said biological material. The polymer matrix is then crosslinked to produce a stabilized layer of crosslinked polymer matrix with a controllable porosity. Again, the biological material can be free, encapsulated or support bound prior to coating with crosslinked polymer matrix. Preferably, the biological material is encapsulated in a first composition prior to coating with the crosslinked polymer matrix.

In a further embodiment, the present invention provides methods of treating disorders that are characterized by the absence of a particular biological function in a patient. The methods comprise introducing into a patient, an encapsulated composition of biological material capable of performing the particular absent biological function, the material being encapsulated according to the methods of the present invention. In preferred aspects, the encapsulated biological material is pancreatic islet cells and the method is used to treat diabetes mellitus.

In another embodiment, the present invention provides a method of culturing cells. The method comprises coating the cells with a layer of crosslinked, mixed functionality, polymer matrix according to the methods of the invention, and culturing the cells.

DESCRIPTION OF THE PREFERRED EMBODIMENT

I. Introduction

Figure 1A:
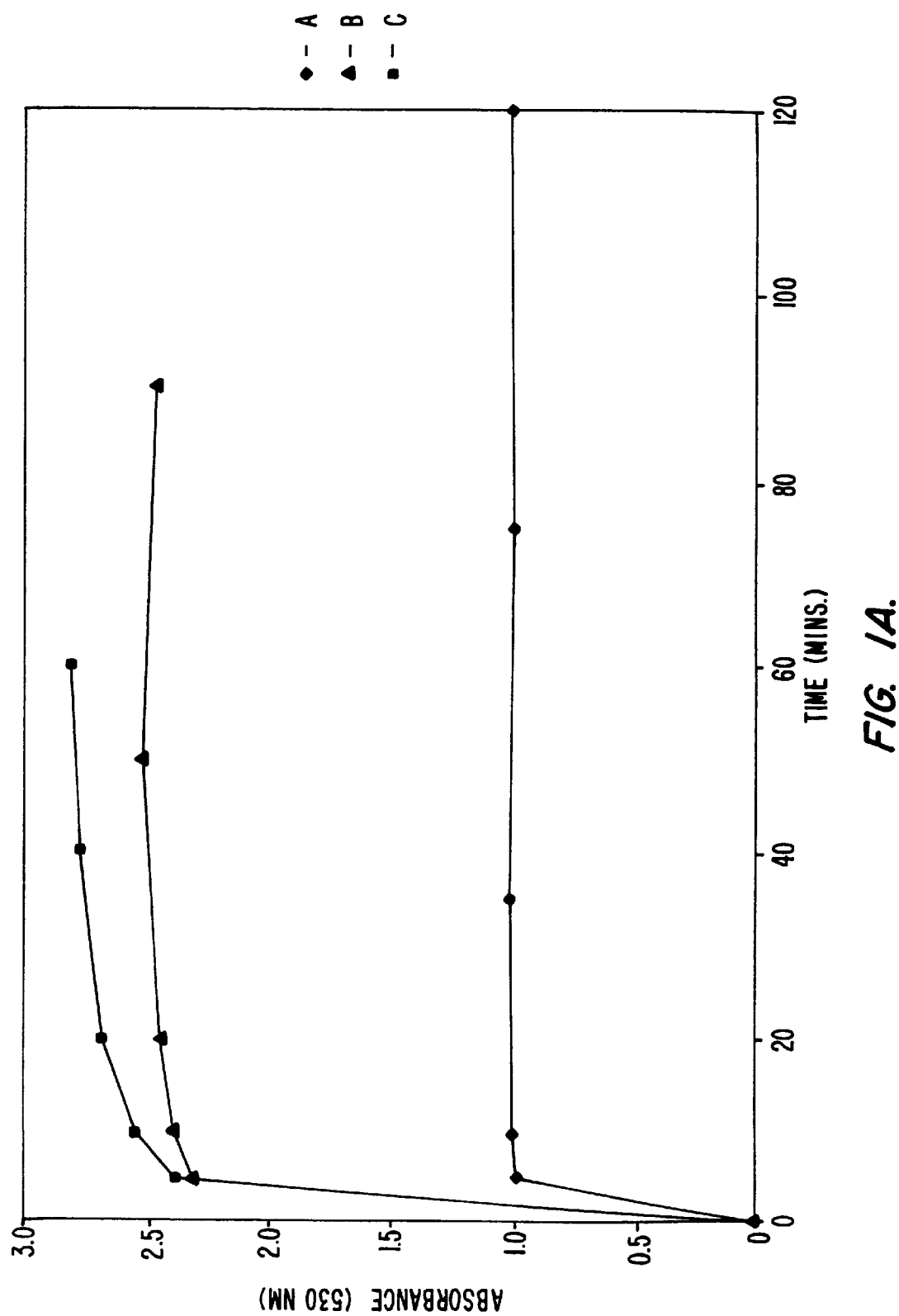
FIG. 1A shows the nucleation of acid soluble Type-I collagen at pH 6.6–6.9 over time, measured as absorbance at 530 nm. Line A shows nucleation of $H_2O$ dialyzed acid soluble collagen (Vitrogen® 100 in 0.012 N HCl, Collagen Corp.). Line B shows nucleation of collagen dialyzed against dilute acetic acid. Line C shows nucleation of collagen having a higher level of sodium acetate than line B.

The present invention generally provides novel, stabilized, microcapsule compositions, and methods for making same. These compositions and methods are characterized by the presence of a layer of stabilized, crosslinked, mixed functionality, polymer matrix. The compositions of the present invention find a variety of uses, including use as protective compositions in cell culturing, and for providing immune barriers for implants and transplantation of exogenous biological material into a host. The methods of the invention have the advantage of being capable of being partially or totally carried out in solution. This advantage eliminates the need for extraneous devices for the encapsulation process, such as electrostatic droplet generators, extrusion droplet generators, and the like. The use of these apparatus may add equipment and process costs to the overall encapsulation process. Additionally, forces associated with these process, e.g., shear, may potentially harm more sensitive materials which are to be encapsulated, e.g., tissue samples and animal cells. See, e.g., Hu, et al., Biotech. and Bioeng. 27:585–595 (1985), Sinskey, et al., Ann. N.Y. Acad. Sci. 369:47–59 (1981).

Further, the compositions of the invention provide improved barriers to immune responses. This may be desirable, for example, where the composition comprises material which is to be implanted or transplanted into a mammalian host. The improved barrier is more resistant to immunological responses which may damage or inactivate the implants, transplants or otherwise harm the host. Additionally, the compositions of the present invention provide a microcapsule composition which has a controllable porosity, allowing alteration of the composition to suit a variety of needs and applications. Furthermore, the compositions of the present invention also provide improved structural properties which increase the durability of the microcapsule composition. These structurally improved compositions are easier to handle and manipulate, and are less likely to be damaged by physical forces, such as shear and abrasion.

II. Microcapsule Compositions

The term "encapsulation" as used herein generally refers to the retention of a composition or area within a compartment, delineated by a physical barrier. For example, the encapsulated biological materials described herein, refer to biological materials which are retained within, and surrounded by a physical barrier. Thus, included within the term "encapsulation," are compositions which are coated, insofar as the coating provides a physical barrier. The term "microcapsule" as used herein, refers to an encapsulated composition, wherein the composition exists as encapsulated beads., each bead ranging in size from about 3 µm to about 2 mm in diameter. More preferably, such beads range from about 50 µm to about 300 µm in diameter.

"Stabilized microcapsule" refers to microcapsules which have been made to withstand normal stresses of the environment to which they will be subjected. For example, a stabilized encapsulation composition will be relatively insoluble and nonreactive with the environment into which it will be introduced.

A. Crosslinked Polymer Matrix Coating

The microcapsule compositions of the present invention are characterized by the presence of a stabilized, crosslinked, mixed functionality polymer matrix layer. The mixed functionality polymers of the present invention refer to long chain polymeric compounds which possess both positively and negatively charged groups. The polymers will also be characterized by their ability to form fibrous aggregates, and nucleate around macroscopic particles at around neutral pH. In particular, such nucleation should occur at from about pH 4.0 to about pH 11.0. Preferably, nucleation should occur at from about pH 5 to about pH 9.0. Examples of mixed functionality polymers which are useful in the present invention include, for example, collagen, synthetic collagen-like polypeptides, derivatized polysaccharide polymers, e.g., alginate, or other derivatized polymers which will self assemble into a macromolecular complex.

One problem associated with many gel matrices used as encapsulation compositions, is their inability to remain as a stable microcapsule composition. The dissolution or disintegration of the microcapsule composition can lead to the rapid exposure of the encapsulated material to the environment outside the microcapsule. This can in turn lead to inactivation or dispersion of the material, defeating the purpose of the composition. However, the crosslinked polymer matrix layer in the compositions of the present invention results in a stabilized microcapsule which resists such dissolution or degradation. Coating with the stabilized polymer matrix herein described, rather than a gel matrix, generally results in a more rigid encapsulation composition than those previously described, e.g., alginate ion-paired gels alone. These enhanced structural properties result from a more rigid coating polymer, as well as the crosslinking within that polymer.

"Crosslinking" as used herein, refers to the linking of two or more chains of polymer molecules, by the formation of a bridge between the molecules composed of either a chemical bond, an element, a group or a compound. The crosslinking generally provides improved structural characteristics and immune barriers. Crosslinking is discussed in greater detail, below.

An added advantage of the crosslinked polymer matrix layer used in the present invention is the ability to control the porosity of that layer. By controlling the porosity of the layer, the composition may be adjusted depending upon the particular application for which it is to be used. Specifically, the porosity may be adjusted to either retain or exclude molecules of a certain size from the composition. For example, where the composition is to be implanted in a mammalian host, it will be desirable to create a barrier to antibodies and complement proteins produced by the host. The barrier may be then adjusted to exclude antibody and/or complement sized proteins. Alternatively, where one wishes to retain proteins or molecules of a certain size within the composition, the porosity may be adjusted accordingly. The porosity of the compositions of the present invention will preferably be such that the compositions have restricted diffusion kinetics for molecules larger than about 20,000 daltons.

Generally, the porosity of the coating layer may be adjusted by varying the level of polymer matrix coating applied, the level of crosslinking, or by mixing in varying amounts of alternative polymers to promote or detract from the matrix integrity. The relative porosity of the crosslinked polymer matrix layer will be inversely related to the coating thickness and/or the level of crosslinking in that coating.

In addition to adjusting the porosity of the coating, one may also adjust the strength of that coating by adjusting the level of crosslinker. For example, where the coated material will be exposed to shear or abrasive forces, higher levels of crosslinking may be desired, e.g., for tissue culture applications. Material which is less likely to encounter such forces, on the other hand, may have a lower level of crosslinking.

B. Collagen Coating

In a preferred aspect of the present invention, the stabilized, crosslinked, mixed functionality, polymer matrix comprises collagen. Collagen is a major protein component of bone, skin, cartilage and connective tissue in animals. In its native form, collagen exists as a trimer of polypeptide chains, termed α-chains, wound around one another in a regular right handed superhelix generating a collagen molecule about 300 nm long and 1.5 nm in diameter. Each a chain is arranged as a left handed helix with three amino acid residues per turn, with a glycine occurring every third residue. The structure of a collagen α chain is thus Gly-X-Y, where X and Y can be any amino acid but one of which is usually proline. In the natural triple helical structure of collagen, the glycine residue occupies the core region of the molecule.

The collagen polypeptides are also generally characterized by a long midsection bounded at either end by the "telopeptide" regions, which constitute less than about 6% of the molecule. These telopeptide regions are generally responsible for lateral and longitudinal assemblage of microscopic and macroscopic prefibrils, fibrils or filaments. The elimination of the telopeptide regions primarily affects the ability of collagen molecules to assemble into macroscopic structures. They also participate in fibril/filament stabilization in that the telopeptides are sites of crosslinking. However, intrahelical crosslinking is more significant. Collagen exists in a number of types having varying physical properties, the most abundant being types I–III.

Collagens useful in the practicing of the present invention will generally be capable of self assemblage. Preferably, this self assemblage will occur at or around neutral or relevant pH. The "relevant pH" may vary depending upon the nature of the biological material to be encapsulated or the biological environment into which the composition is to be introduced. For example, in most mammalian applications, the relevant pH will be approximately neutral. However, where the material to be coated is not amenable to pH outside either the basic or acidic range, it may be desirable to use a collagen which will allow coating in this range. similarly, where the environment into which the composition is to be introduced is within the acidic or basic range, it may be desirable to provide a collagen coating which will remain insoluble within this range.

Acid soluble forms of collagen prepared by pepsin digestion of the native collagen may be particularly useful in practicing the present invention. These soluble collagens are generally commercially available. For example, Type-I collagen in an acid soluble, pepsin extracted form is commercially available as Vitrogen® 100, from Collagen Corp., in 0.012N HCl. Although acid soluble Type-I collagen is preferred for the methods and compositions of the present invention, those of skill in the art will recognize that a number of collagen forms may be used in practicing the present invention. For example, U.S. Pat. No. 4,164,559 to Miyata, et al., reports the alteration of the pH profile of fibril formation by varying the derivatization of the collagen. The collagen forms therein described may be applicable where the relevant pH for a particular encapsulated composition is lower or higher than the neutral range.

The use of collagen matrices has been reported in the culturing of islet cells. Specifically, Chao, et al., *Cell Transplantation* 1:51–60 (1992), discusses the use of three-dimensional collagen gel matrices in culturing of islet cells. Suspension of islet cells in large collagen gel matrices prevented cell adhesion to culture vessels, thus improving retrieval rates of islet cells. This also obviated the need for mechanical dislodging of the cells from the culture vessel, which often results in disintegration of the islet cells. Similarly, Ohgawara et al., *In Vitro Cell. Dev. Biol.* 26:348–352 (1990) report the use of similar collagen matrices in the long term culturing of pig pancreatic pseudoislets.

As already discussed, collagen is not soluble at neutral pH in its naturally existing form. However, modification of collagen, e.g., pepsin extraction or chemical modification, produces a cleaner collagen which has better solubility characteristics, as well as reduced antigenicity/immunogehicity due to the reduced telopeptide content. Many commercially available forms of collagen are prepared by this method, and are available as sterile filtered, acid soluble collagen solutions. As with many soluble proteins, the solubility of these collagens is dependent upon a number of factors, including pH, temperature, molecular weight of the predominant form of collagen present, protein concentration and salt concentration in the solution. Another factor affecting solubility can be the presence of particulate matter in the solution. Such particulate matter can become a site of nucleation for proteins which are moderately soluble. Without being bound to a particular theory, it is believed that the material to be coated using the methods described herein provides a macroscopic nucleation site for the collagen.

Accordingly, the methods of the present invention provide for the coating of the biological material by taking advantage of the natural properties of the collagen solution used. In particular, biological material, whether encapsulated, support bound or a free particulate, is introduced into a solution of collagen. The conditions of the solution may be adjusted whereby the collagen begins to form into fibrils, and nucleate around the biological material. Specifically, the pH, salt concentration, temperature and/or the concentration of collagen may be selected or adjusted to control the initiation rate, extent and quality of fibril formation. The particular conditions adjusted and the range of these adjustments may depend upon a number of factors, including, for example, the sensitivity of the material to be encapsulated to changes in pH, temperature and salt concentration.

Acid soluble forms of collagen peptides generally begin to associate in solution when the pH of that solution approaches neutral pH. These associated collagen peptides, or fibrils, readily precipitate out of solution. For example, Vitrogen collagen solutions tend to become viscous at pH 4.5 due to preassembly of collagen fibrils, and readily precipitate at pH 5 and greater. This association, or fibril formation may be further enhanced in the presence of macroscopic particles which act as sites for nucleation of fibril formation. Commercially available collagen (Vitrogen®-100) is available as a 0.3% solution w/v. However, it may be appreciated that the concentration of the collagen solution used in practicing the present invention may be readily varied depending upon the solubility of the collagen and the amount of material to be coated. In preferred aspects of the present invention, collagen solutions having a concentration from 0.03% to about 5% collagen w/v may be used, with 0.3% being most preferred.

As described, collagen nucleation is also affected by pH and acid/salt concentrations. In particular, organic acids/salts generally inhibit, or slow fibril formation, resulting in increased solubility of collagen, while inorganic salts, e.g., NaCl, tend to accelerate fibril formation resulting in more rapid precipitation of the collagen. Slowing of fibril formation may allow for the assembly of larger fibrils which in turn will impart a greater structural integrity on an encapsulated composition (See FIG. 1). As such, it may be desirable to provide the collagen in a solution of organic acid/salt, e.g., acetate, and lacking appreciable amounts of inorganic salts, e.g., chloride.

In addition to adjusting the conditions of collagen nucleation, it may also be desirable to adjust the level of collagen coating applied to the biological material according to the methods of the present invention. Because the amount of coating is related to the surface area of the material to be coated, the amount of total collagen added in the coating process will likely vary depending upon the nature of the material to be coated. For example, where the material to be coated comprises small particles, e.g., alginate microcapsules or beads, ranging in size from about 50 to about 250 μm in diameter, collagen may be added at from about 0.2 to about 2.0 g collagen/ml packed bead volume. For larger size particles, or a thinner collagen coating, lower levels of total collagen may be added, while a thicker coating or smaller particle sizes (having greater surface area per ml packed bead volume) may utilize more total added collagen.

The crosslinked collagen matrix may be further adjusted through the addition of alternative polymers, added concurrently with the collagen polymers, which enhance, or alternatively, detract from the integrity of the resulting matrix. For example, additional crosslinkable polymers may provide a substantial enhancement to the integrity of the matrix, much like interlocking puzzle pieces. Alternatively, the integrity of the matrix may be reduced by the inclusion of polymers which act as spacers between collagen fibrils reducing the level of crosslinking.

As discussed previously, collagen fibril formation is enhanced in the presence of inorganic salts, and inhibited in the presence of organic acids/salts. As commercially available collagen preparations are generally provided in HCl solutions, it may therefore be useful to exchange the hydrochloric acid with an organic acid. This exchange can be carried out by a variety of means, including, e.g., dialysis, gel filtration and diafiltration. Preferred collagen solutions will be in a dilute acetic acid solution at about pH 4.5 (deionized water adjusted to pH 4.5 with acetic acid). At pH 4.5, the collagen solution will generally be somewhat viscous due to preassembly of the fibrils. Adjustment of the pH of the collagen solution to greater than pH 5 results in fibril formation and protein nucleation. The nucleation of collagen at around neutral pH makes it particularly suitable for coating biological materials which are sensitive to extremes of pH. Therefore, typically, the initiation of collagen nucleation is carried out by adjusting the pH of the collagen solution to greater than about pH 4. Preferably, the pH is adjusted to between about pH 5 and pH 8.0, and most preferably, from about pH 6.5 to about pH 6.9.

Collagen proteins have a reported isoelectric point of between about 8.5 and 10. Thus, at nucleation pH, e.g., between 5 and 8, the collagen peptides will generally carry a net positive charge. Accordingly, it will be appreciated that in preferred methods, the biological material to be coated may carry a net negative charge. The differences in net charges between the collagen and functional groups on the material around which nucleation is desired may enhance nucleation around the biological material.

In addition to commercially available collagen types, it may also be appreciated that derivatized collagen may also be used in the methods of the present invention. Polymer derivatization is well known in the art, and may allow for the alteration of the properties of the particular polymer used, e.g., improved nucleation, better stability of crosslinked forms, alteration of nucleation pH profiles, etc. Examples of derivatized collagen include pegylated collagen (collagen to which polyethylene glycol has been covalently attached), succinylated collagen, alkylated collagen (e.g., methylated), aminated collagen, activated aldehyde derivatized collagen, and the like. See, e.g., U.S. Pat. No. 4,164,559.

C. Other Polymers Matrices

Although the present invention is primarily described in terms of a collagen coating, it may also be appreciated that a variety of other polymers may be used. For example, polymers which possess similar characteristics to the collagen compositions herein described may be particularly useful. Of particular interest are those polymers which are soluble in the acidic pH or basic pH, but precipitate at around neutral or relevant pH, allowing for nucleation of the polymer around the material to be coated. More preferred would be those polymers which form fibrous aggregates, and have a net charge opposite to the material being coated, at neutral pH. For example, synthetic peptides or other polymers which comprise structures similar to the amino acid sequence of collagens may be applied in the methods and compositions of the present invention. Specifically, the structure of the collagen triple helix results in the smaller glycine, proline and hydroxyproline molecules being in the core of the helix while larger amino acids, e.g., positively charged residues, such as lysine, and negatively charged residues, such as aspartic or glutamic acids, being positioned on the outer portions of the trimer. This results in a polymer having alternating positive and negative charges on its surface. Polypeptides may generally be prepared either synthetically, or recombinantly for use in the present invention. In general, techniques for recombinant production of polypeptides are described, for example, in Sambrook et al., *Molecular Cloning: A Laboratory Manual* (2nd ed.) Vols. 1–3, Cold Spring Harbor Laboratory, (1989). Techniques for the synthesis of polypeptides are generally described in Merrifield, *J. Amer. Chem. Soc.* 85:2149–2456 (1963), Atherton, et al., *Solid Phase Peptide Synthesis: A Practical Approach*, IRL Press, Oxford (1989), and Merrifield, *Science* 232:341–347 (1986).

In another aspect, the stabilized crosslinked polymer matrix may comprise a derivatized polysaccharide polymer, preferably an alginate polymer. The derivatized alginate polymers of the present invention are characterized by mixed anionic and cationic groups within each polymer chain, similar to the alternating charges of the collagen molecules.

D. Crosslinking Following the application of the polymer matrix layer, the layer may be crosslinked to stabilize that layer. The type of crosslinker used will generally depend upon the type of polymer used in the coating process. Zero-length crosslinkers are preferred for the practicing of the present invention. A "zero-length crosslinker" refers to a crosslinking compound which will mediate or produce a direct crosslink between functional groups of two polymer molecules. For example, in the crosslinking of two proteins, a zero-length crosslinker will result in the formation of a bridge, or crosslink between a carboxyl group from an amino acid side-chain of one protein, and an amino group of another, without integrating foreign material. Particularly useful crosslinkers effect the crosslinking via a condensation reaction liberating water, ammonia or an amine containing compound, an alcohol or other simple group. Such crosslinkers are termed condensable crosslinkers.

In preferred aspects of the present invention, where collagen is the polymer of choice, a number of organic crosslinkers, well known in the art may be used. Carbodiimides are particularly useful as protein crosslinkers and are preferred in the practicing of the present invention. In particular, carbodiimides may crosslink a carboxyl group of one protein with an amino group of another protein via a condensation reaction, resulting in crosslinked protein and an isourea. However, the nature of most carbodiimides as only soluble in organic solvents may preclude their use in many biological applications. Thus, organic soluble crosslinkers may be used so long as the solvent effects can be tolerated by the biological material. Accordingly, the present invention, in a more preferred aspect, provides for the crosslinking of the collagen layer using a water soluble carbodiimide. A still more preferred crosslinker is 1-ethyl-3-(3-dimethylaminopropyl) carbodiimide hydrochloride ("EDC").

The amount of crosslinking reagent can vary depending upon the amount of surface area to be crosslinked. For example, a composition comprising twice the amount of polymer matrix, e.g., collagen coating, will generally require two times the amount of crosslinking reagent. Alternatively, use of two times the crosslinking reagent may reduce the time required for crosslinking by half. Additionally, the amounts of crosslinking reagent and/or crosslinking time may be adjusted to increase or decrease the level of crosslinking, depending upon the individual requirements for the coated material. Of particular importance is the ability to adjust the porosity of the coating polymer matrix through the adjustment of the amount of crosslinking in that coating. For example, by increasing the level of crosslinking, one reduces the porosity of the coating, whereas by decreasing the level of crosslinker, one increases that porosity.

Similarly, as described previously, the matrix may comprise additional polymers which may or may not be crosslinked, resulting in an enhanced or reduced integrity matrix. The use of these alternate polymers may be adjusted in conjunction with the level of crosslinker to achieve the desired porosity of the matrix.

E. Determination of Coating Effectiveness

A variety of methods may be used in determining the effectiveness of the coating process and layer. For example, the porosity of a layer resulting from a particular coating process may be determined by applying a coating of crosslinked polymer matrix to encapsulated red blood cells. The RBCs may be suspended in appropriate media which may then be assayed for the presence of hemoglobin or cells outside the microcapsules. Coating efficiency may also be determined visually using, e.g., a microscope, and counting the number of coated and uncoated particles, beads or cells in a representative sample.

The effectiveness of the coating process may also be determined by incubating the coated/encapsulated composition with an antibody and/or complement proteins, to the biological material within the composition, and detecting antibody binding to the biological material. Antibody binding may be shown, for example, by antibody induced lysis of cells, or by the presence of labelled antibody bound to the biological material.

Alternatively, the integrity of a coating may be determined by standard equilibrium dialysis methods.

III. Encapsulated Biological Material

In a preferred aspect, the stabilized microcapsule compositions of the present invention will generally comprise biological material within the microcapsule.

"Biological material," as the phrase is used herein, is defined as any material of biological origin which possesses a biological activity. For example, biological material-would include cells, i.e., bacterial, fungal, mammalian, insect, plant, etc. Also included within the definition of biological material are proteins, enzymes, cell fragments, organelles, or the like. Typically, the biological material will comprise cells, wild type or genetically engineered, and preferably, pancreatic islet cells.

Without being bound to a particular theory, it is believed that the biological material provides a suitable nucleus around which collagen fibrils may form. Accordingly, the methods of the present invention may be used to apply a stabilized crosslinked polymer matrix around any particle. For example, in some instances, the biological material may be directly coated with crosslinked polymer matrix according to the methods of the present invention, i.e., tissue samples, individual cells, etc.

However, it also may be desirable in some instances to provide the biological material as a component of another composition, such that it will serve as a suitable site/particle for nucleation of the polymer matrix. For example, where it is desired to encapsulate proteins, enzymes or other soluble biological materials using the methods of the present invention, it may be necessary to attach the protein or enzyme to a suitable solid support. The support bound material may then be coated with a crosslinked polymer matrix using the methods of the invention. Suitable solid supports include those generally well known in the art, for example, cellulose, agarose, silica, starch, divinylbenzene, polystyrene, or the like.

In the case where the biological material consists of cells or cell fragments, it should also be appreciated that a suitable solid support may also be used. Alternatively, such biological material may be encapsulated in a first composition to form a gel particle, prior to coating with the crosslinked polymer matrix.

A. Coating of Encapsulated Biological Material

In a preferred embodiment, the biological material is encapsulated in a first composition, prior to coating with crosslinked polymer matrix. In more preferred aspects, the biological material is encapsulated in a first composition of alginate gel, prior to polymer matrix coating. The biological material to be coated, whether encapsulated, support bound or free, will generally be relatively small. For example, in the case of encapsulated biological material, individual capsules will generally be from about 20 $\mu$m to about 200 $\mu$m in diameter prior to collagen coating. Similarly, support bound biological material will generally be from about 20 $\mu$m to about 200 $\mu$m in diameter, including the support. Free biological material, e.g., cells or tissue samples may range in size from an individual cell, e.g., ~1 $\mu$m, to tissue samples which comprise a number of cells and can be as large as 200 $\mu$m to 2 mm in diameter, prior to collagen coating.

Alginates are linear polymers of mannuronic and guluronic acid residues which are arranged in blocks of several adjacent guluronic acid residues forming guluronate blocks and blocks of adjacent mannuronic acid residues forming mannuronate blocks, interspersed with mixed, or heterogenous blocks of alternating guluronic and mannuronic acid residues. Generally, monovalent cation alginate salts are soluble, e.g., Na-alginate. Divalent cations, such as $Ca^{++}$, $Ba^{++}$, $Sr^{++}$, or $Fe^{++/+++}$ tend to interact with guluronate, and the cooperative binding of these cations within the guluronate blocks provides the primary intramolecular crosslinking responsible for formation of stable alginate gels.

In some aspects of the present invention, it may also be desirable to use alginate gels which are nonfibrogenic. This is particularly the case where the encapsulated biological material is to be implanted in a mammalian host. Fibrogenicity of alginates is generally attributed to contaminating fucan and polyphenol rich physoides and other particulate contaminants. These contaminants may be purified away from the alginate to reduce its fibrogenicity. See, e.g., Published PCT Application No. 93/24077.

Encapsulation of biological material in an alginate gel may be carried out by a variety of methods. Typically, such encapsulation methods consist of suspending the biological material in a first solution of a monovalent cation salt of alginate, e.g., sodium alginate. Droplets of the alginate solution containing the biological material are then generated in air. Droplet generation may be carried out using any droplet generation device. For example, droplets may be generated by gravitational flow from a tube or needle into air, where the effects of surface tension result in the formation of spherical droplets of the suspension. Alternatively, electrostatic droplet generators may be used whereby an electrostatic differential is created between an alginate solution and the collection solution, such that the alginate is drawn through a tube or needle in small droplets. Other devices are equally applicable, including the use of a spinning disc droplet generator or laminar air flow extrusion device. See Goosen, *Fundamentals of Animal Cell Encapsulation*, CRC Press (1993), U.S. Pat. No. 5,286,495.

Once generated, the droplets are then collected in a separate solution comprising divalent metal cations, e.g., $Ca^{++}$, $Ba^{++}$ or $Sr^{++}$. Generally, $CaCl_2$, $BaCl_2$ and $SrCl_2$ solutions are preferred, with $BaCl_2$ being most preferred. The droplets are gelled by the interactions between the alginate and the divalent cations in the collection solution, entrapping, or encapsulating the biological material suspended within the gelled alginate droplets.

In an alternative method, alginate encapsulation may be carried out in solution according to the methods as described in substantial detail in copending U.S. patent application Ser. No. 08/399,698, filed Mar. 3, 1995 and now abandoned (Attorney Docket No. 16325-13). According to these methods, alginate encapsulated biological material may be carried out entirely in solution, without the necessity of generating droplets in air. Thus, no droplet generating devices are required.

Briefly, according to the alternate alginate encapsulation methods, the biological material, as defined herein, may be saturated or suffused with a solution of divalent metal cations. The free (unbound) cations are washed from the surface of the biological material which is then suspended in a solution of sodium alginate. The differential in the level of divalent cations in the biological material and the surrounding alginate solution will result in the radial diffusion of the cations from the biological material into the alginate solution, gelling the alginate and resulting in the formation of an alginate barrier surrounding the biological material, which may then be cured by further treatment with a divalent cation solution. See U.S. patent application Ser. No. 08/399,698, filed Mar. 3, 1995 and now abandoned.

The alginate encapsulated materials then may be coated with a polymer matrix which is then crosslinked, according to the methods of the present invention, or, alternatively, may be further treated to stabilize their structure. Further treatments to stabilize the alginate structure include those generally known in the art, e.g., multiple alginate coatings, and/or polylysine coating, and the like. See, e.g., *J. Pharm. Sci.* 70:351–354 (1981) and U.S. Pat. No. 5,286,495.

B. Final Overcoating of Biocompatible Polymer

Following crosslinking of the polymer matrix layer, the composition may optionally comprise an additional layer of a biocompatible polymer matrix, coating the crosslinked polymer matrix layer. The term "biocompatible polymer" refers to a polymer which is nontoxic or otherwise not harmful to mammalian systems. Examples of biocompatible polymers include nonfibrogenic forms of alginate, as well as polyethylene glycol and liposomal formulations. This further layer of biocompatible polymer may be particularly desirable where the composition is to be introduced into a mammal which may have an immunogenic response to the crosslinked polymer matrix coating.

In a preferred aspect, the compositions of the present invention comprise a further layer of a biocompatible alginate gel. Biocompatible alginate gels are as substantially described above. This further alginate layer may be applied according to the alginate encapsulation methods described previously.

III. Other MicrocaPsule Compositions

It should also be appreciated that the methods of the present invention may be applied in the preparation of hollow microcapsules. In particular, a layer of a crosslinked polymer matrix, e.g., collagen, may be formed around a bead. Following crosslinking, the internal bead structure may be solubilized and extracted from the interior, leaving the crosslinked polymer shell or microcapsule. As a specific example, following coating of a calcium-alginate bead, as described above, with a layer of collagen, the alginate bead may be solubilized and removed from the collagen shell. Solubilization of Ca-alginate may be carried out, for example, by chelating the calcium cation which was used in gelling the alginate initially. Ethylenediaminetetraacetic acid ("EDTA") or ethylene glycol bis-(β-aminoethylether)-N,N-tetraacetic acid ("EGTA") is particularly useful for chelating calcium and other divalent cations. Once the alginate gel is dissolved, it can be readily removed from the capsule's interior, e.g., by dissipation into the surrounding medium. The result is a hollow crosslinked collagen shell. The crosslinked collagen shell or microcapsule may then be used in a variety of applications, e.g., pharmaceutical formulation for drug delivery systems, or alternatively, may be subject to further processing, such as, the addition of further alginate or collagen coatings.

In a related aspect, it may be desirable to create collagen coated biological material absent an alginate encapsulated core. For example, the collagen microcapsule may be formed around cells which have a survival requirement for attachment to suitable surfaces. For example, hepatocytes and other primary cells have been shown to prefer collagen over modified plastics as a growth promoting and sustaining cell culture surface. The cells are first encapsulated in Ca-alginate gel, followed by coating with a crosslinked polymer matrix, e.g., collagen. Dissolution of the Ca-alginate gel will thus yield a crosslinked collagen microsphere, which contains the cells in question, having a defined porosity, and a preferred cell attachment surface, and with an optional external layer of alginate.

IV. Uses for Encapsulated Biological Materials of the Present Invention

The improved ability of the encapsulated compositions of the present invention to resist destruction by immune responses, as well as their improved structural characteristics, make these compositions useful in a variety of industrial and therapeutic applications.

A. Encapsulation of Transplantable Biological Material

The encapsulation compositions of the present invention are particularly useful in transplant therapy. The term "transplant" broadly refers to the introduction of exogenous biological material into an animal, herein referred to as a "host" or "patient." The exogenous material may be. derived from a different location within the same host, or may be derived from a separate animal, termed the "donor." Donors and hosts may be of the same or different species. Transplants from the same species are termed allografts while those between two separate species are termed xenografts. Typically, for transplants between two separate animals of the same or differing species, it will be desirable to provide a transplantable composition having enhanced immune protection for the transplanted material. The compositions of the present invention are particularly useful in these applications. Additionally, the transplant composition itself, cannot cause a significant immune response in the host. Accordingly, when used in transplant therapy, the encapsulated compositions of the present invention will generally comprise an additional layer of alginate gel over the crosslinked polymer matrix layer. More preferably, the biological material to be transplanted, e.g., cells, will be encapsulated in a first alginate gel which will then be coated with the crosslinked polymer matrix layer followed by a second layer of alginate gel.

Preferred tissues suitable for the transplantation methods of the present invention include secretory organ tissues, where transplantation from a donor organ to a host, is intended to replicate the donor organ's function in the host thereby replacing or augmenting that function in the host. While the skilled artisan will recognize the utility of the methods of the present invention in transplantation of a variety of tissue types, particularly preferred donor organ tissues include pancreatic islet cells, hepatic cells, neural cells, renal cortex cells, vascular endothelial cells, thyroid cells, adrenal cells, thymic cells and ovarian cells.

Both wild type and recombinant cell lines which express a function lacking or deficient in the host may also be incorporated into the methods of the present invention, whereby their introduction into the host will replace that lacking or deficient function.

In a particularly preferred example, the transplantation methods of the present invention relate to the transplantation of pancreatic islet cells. Preferred sources of islet cells include, e.g., human, subhuman primate, porcine, bovine, rabbit, rat, mouse and the like, with human and porcine islets being most preferred.

The transplantation of islet cells, as described herein, may be particularly useful in treating a patient suffering from diabetes mellitus. In particular, the method of treatment comprises the introduction into the patient of an effective amount of islet cell xenografts or allografts, encapsulated according to the methods of the present invention. An effective amount is defined as an amount of encapsulated cells which, when introduced into a diabetic patient, will result in the normalization of blood glucose levels of that patient. Precise effective amounts will generally depend upon the size of the patient, and the severity of the particular disorder to be treated. Typically, such effective amounts may comprise an excess of the encapsulated composition, in order to ensure a sufficient amount of the transplant material to effect treatment.

Implantation of the encapsulated compositions is typically carried out by simple injection through a hypodermic needle having a bore diameter sufficient to permit passage of a suspension of the encapsulated material without damaging the composition. Implantation may also be carried out using an open procedure, or by other methods known in the art. The particular implantation method may vary depending upon the material to be implanted, and the desired location of the implant.

For implantation, the encapsulated compositions of the present invention will typically be formulated as a pharmaceutical composition. In particular, the composition will generally be formulated together with one or more pharmaceutically or therapeutically acceptable carriers and optionally other therapeutic ingredients. Various considerations are described, e.g., in Gilman et al. (eds) (1990) *Goodman and Gilman's: The Pharmacological Bases of Therapeutics*, 8th Ed., Pergamon Press; *Novel Drug Delivery Systems*, 2nd Ed., Norris (ed.) Marcel Dekker Inc. (1989), and *Remington's Pharmaceutical Sciences*, the full disclosures of which are incorporated herein by reference. Pharmaceutically acceptable carriers will include water, saline, buffers and other compounds described in, e.g., the Merck Index, Merck and Co., Rahway, N.J.

B. Cell Culturing

Improved structural integrity of the microcapsule compositions of the present invention also provides advantages useful in cell culturing methods. The encapsulated compositions are particularly useful where cells are incompatible with typical cell culturing methods. This incompatibility may be a sensitivity of the particular cell type to physical forces associated with cell culturing processes and equipment, e.g., agitation, aeration, material handling, and the like. Alternatively, the incompatibility may be a result of a particular property of the cell type in question, such as, adhesion to the culture vessel, or excessive dispersion of the cells. Culturing of pancreatic islet cells, for example, poses a number of obstacles, including dispersion of cells, adhesion to culture vessels, and disintegration upon mechanical agitation. See Chao, et al., *Cell Transplantation* 1:51–60 (1992).

As such, the encapsulated compositions of the present invention are also useful in cell culturing techniques. In particular, cells to be cultured are first encapsulated according to the methods described herein. The encapsulated cells possessing the enhanced structural properties of the encapsulated compositions of the present invention, whether tethered to solid supports or otherwise, may then be cultured according to traditional culturing techniques well known in the art. See, e.g., Feder and Tolbert, Sci. Am. 248:36–43 (1985).

In addition to the above uses, the skilled artisan will recognize that the methods and compositions described herein may also find use in formulation of pharmaceutical delivery systems, for oral or other administration methods.

The present invention is further illustrated by the following examples. These examples are merely to illustrate aspects of the present invention and are not intended as limitations of this invention.

EXAMPLES

Example 1—Collagen Coating

A. Determination of Collagen Nucleation Conditions

Vitrogen-100® solution is commercially available as a 100 ml, sterile filtered, 0.3% collagen solution at pH 2.0 (0.012 N HCl). The vitrogen solution was dialyzed against: (1) dilute acetic acid ("HOAc") at pH 4.5 (HOAc in water to reach pH 4.5), until the solution reached a pH of 4.4–4.6, followed by adjustment of the pH to 3.5 using dilute HOAc (1M) then back to pH 4.5 using dilute sodium hydroxide (NaOH) (1N) (See FIG. 1, Line A); (2) 6 liters of deionized $H_2O$, followed by pH adjustment to 4.5 with 1 N NaOH (See FIG. 1, Line B); (3) dilute HOAc dialysis as in (1), followed by pH adjust to approximately 10 with 1N NaOH, followed by adjustment to pH 6.7 using 1N HOAC (See FIG. 1, Line C). The resulting collagen solution thus contained a higher concentration of sodium acetate than (1). The other collagen solutions were adjusted to pH 6.6–6.9 using 1N NaOH, and collagen nucleation/precipitation was measured spectrophotometrically as an increase in absorbance at 530 nm.

Collagen in dilute organic acid solutions (lines A and C, respectively) showed a higher levels of light detraction (Abs at 530 nm), indicating a greater level of collagen fibril formation, and larger fibrils. Nucleation in the presence of residual chloride (line B) showed a lower level of fibril formation.

Figure 1B:
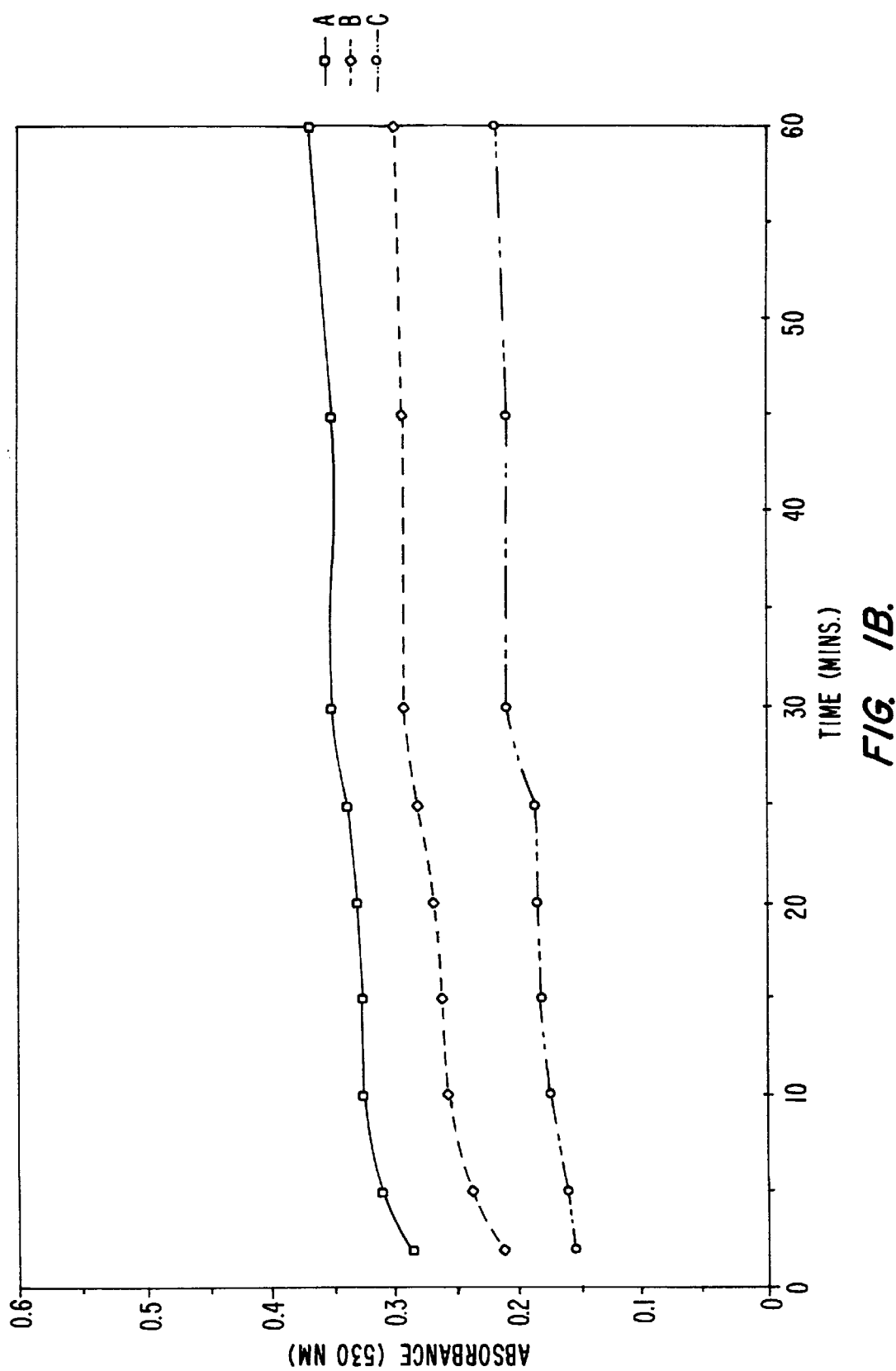
FIG. 1B shows a comparison of differences in nucleation levels of collagen as a function of additional acetic acid added to one gram of dialyzed collagen solution mixed with 1.5 grams 2× sucrose solution (A=0.010 ml added HOAc, B=0.012 ml added HOAc, C=0.014 ml added HOAc).

Vitrogen solution (100 ml) was dialyzed against 6 liters of HOAC, pH 3.5. The dialysis solution was changed four times over 3 days. The spectroscopic nucleation assay requires 1 gram of the dialyzed collagen solution to be mixed with 1.5 grams of the 2× sucrose solution in a cuvette. The pH of the collagen-sucrose solution was adjusted to pH 6.2 with 1 N NaOH and the solution absorbance was monitored. In FIG. 1B, the data compares the change in the level of nucleation as a function of additional added HOAc (A=0.010 ml, B=0.012 ml, C=0.014 ml). The data demonstrates that increasing the concentration of acetate in the nucleation, reaction inhibits the solution dependent assembly of macroscopic collagen fibers. Red blood cells coated with collagen titrated as above were subjected to hemolysis assays, as described in greater detail, below.

B. Collagen Coating Process

A sample of alginate beads comprising encapsulated red blood cells, were washed by suspending the beads in a saline, 2 mM Calcium chloride ("$CaCl_2$") solution. The beads were centrifuged at low speed (1000–2000 rpm) and the supernatant was removed. This wash step was repeated. The beads were then twice washed by suspending in 2× sucrose solution (18.5% sucrose, 2 mM $CaCl_2$), followed by centrifugation and removal of the supernatant.

To the packed bead volume was added a one-half volume of 2× sucrose solution. 0.5 M 2-(N-morpholino)-ethane sulfonic acid buffer ("MES"), pH 6.0, was added to the bead suspension to a final concentration of 0.02 M MES. A 0.25–0.3% collagen solution in dilute acetic acid, at approximately pH 3.4, was added to the bead suspension to achieve an approximate ratio of 1 gm collagen/ml packed bead volume. 1 M NaOH was added to bring the suspension pH to from about 6.2 to about 6.5. The bead suspension was then rotated for 1 hour at room temperature on a test tube rotator.

Following rotation, the bead suspension was diluted with 1× sucrose solution (9.25% sucrose, 2 mM $CaCl_2$, 10 mM MES pH 6.0). The diluted suspension was centrifuged, washed and the supernatant removed so that the packed bead volume made up 1 half of the total volume. 0.1 ml EDC (1-ethyl-3-(-3-dimethylaminopropyl) carbodiimide hydrochloride) solution was added to the bead suspension to yield a final EDC concentration of 1–4 mg/ml packed bead volume. The beads were vortexed immediately, and shaken by hand for 30 minutes. The beads were then diluted in media supplemented with 4 mM $CaCl_2$, 0.5% gelatin. The beads were centrifuged and the supernatant was decanted. The beads were again suspended in media.

C. Assaying Collagen Coated Beads

Collagen coated alginate encapsulated RBCs ("coated beads") were compared against alginate encapsulated RBCs ("uncoated beads") inma variety of tests, and assayed for the release of hemoglobin as an indicator of cell lysis.

Figure 2A:
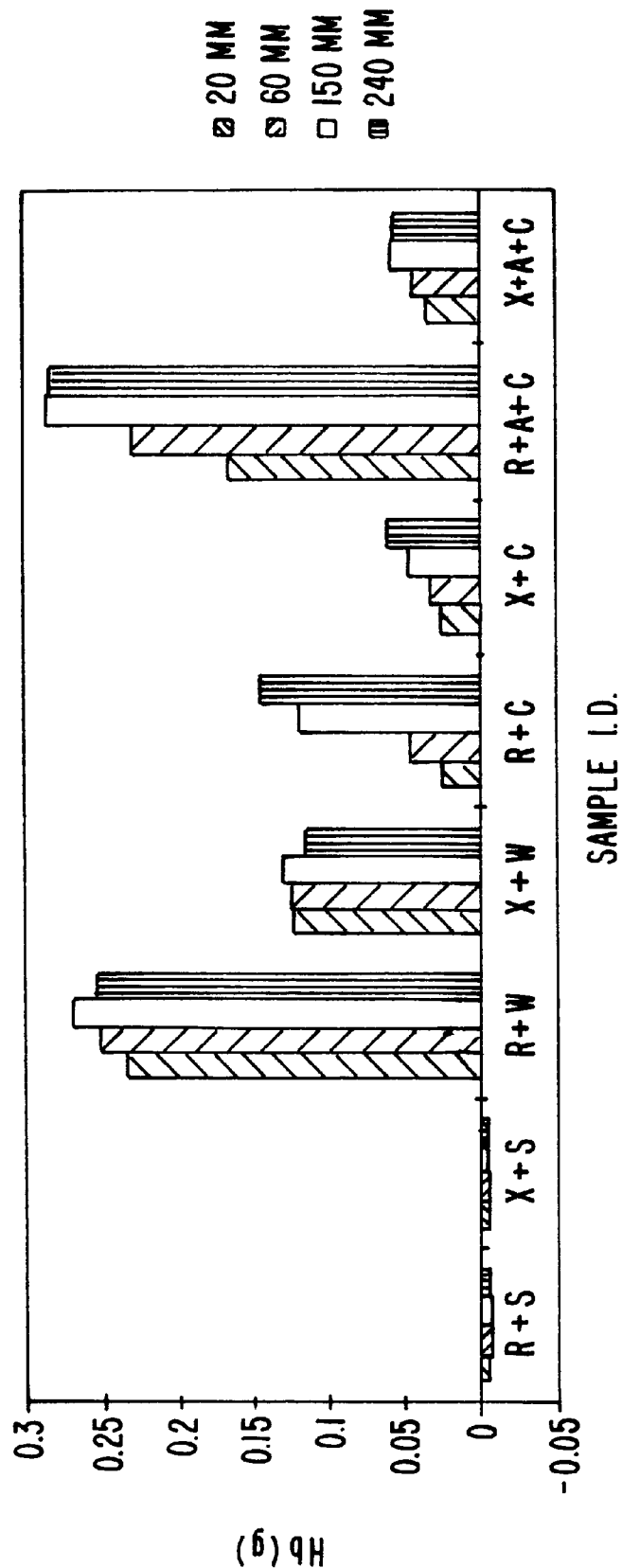
FIG. 2A shows a comparison of hemolysis rates of alginate encapsulated red blood cells ("R"), and collagen coated alginate encapsulated red blood cells ("X"). The different compositions were tested in saline ("S") as a negative control, water ("W"), as a positive control, in the presence of guinea pig complement ("C"), and in the presence of anti-sheep red blood cell antibody plus guinea pig complement ("A+C"). Thus, "X+S" and "R+S" represent collagen coated alginate encapsulated red blood cells and red blood cells that are only encapsulated in alginate incubated in saline, respectively. "R+W" and "X+W" represent alginate encapsulated and collagen coated, alginate encapsulated red blood cells incubated in water, respectively. "X+C" and "R+C" represent collagen coated, alginate encapsulated red blood cells and and alginate encapsulated red blood cells incubated in the presence of guinea pig complement, respectively. "R+A+C" and "X+A+C" represent alginate encapsulated and collagen coated, alginate encapsulated red blood cells incubated with antibody plus complement, respectively. Measurements were taken at 20, 60, 150 and 240 minutes, according to the legend shown.

Approximately 10,000 encapsulated RBC beads were incubated either in saline, in water, in the presence of guinea pig complement, or anti-sheep RBC antibody plus guinea pig complement. Aliquots (0.1 ml) were removed from each treatment at 20 minutes, 60 minutes, 150 minutes and 240 minutes, and diluted with four volumes of Drabkin's reagent for the spectrophotometric measurement of hemoglobin in the supernatant. Beads suspended in saline operated as a negative control, showing no hemolysis during the experiment, while suspension in water constituted a positive control showing nearly complete, immediate hemolysis, as shown in FIG. 2A. As shown, the negative saline control showed no hemolysis for alginate encapsulated RBCs (R+S) or collagen coated, alginate encapsulated RBCs (X+S). Conversely, the positive water control showed near complete hemolysis for both alginate encapsulated and collagen coated, alginate encapsulated RBCs (R+W and X+W, respectively). The reduced hemolysis level in the collagen coated RBCs is believed to be a result of losses occurring during the additional coating process. When incubated with guinea pig complement or antibody plus guinea pig complement ("+C" and "+A+C", respectively), collagen coated RBCs showed distinctly lower levels of hemolysis over time than the RBCs that were only alginate encapsulated. In particular, comparison of collagen coated beads to uncoated beads shows that coated beads are much more resistant to lysis by complement activation than uncoated beads. Similarly, coated beads tend to retard antibody dependent complement lysis as well, whereas the uncoated beads show complete lysis by 150 minutes.

Figure 2B:
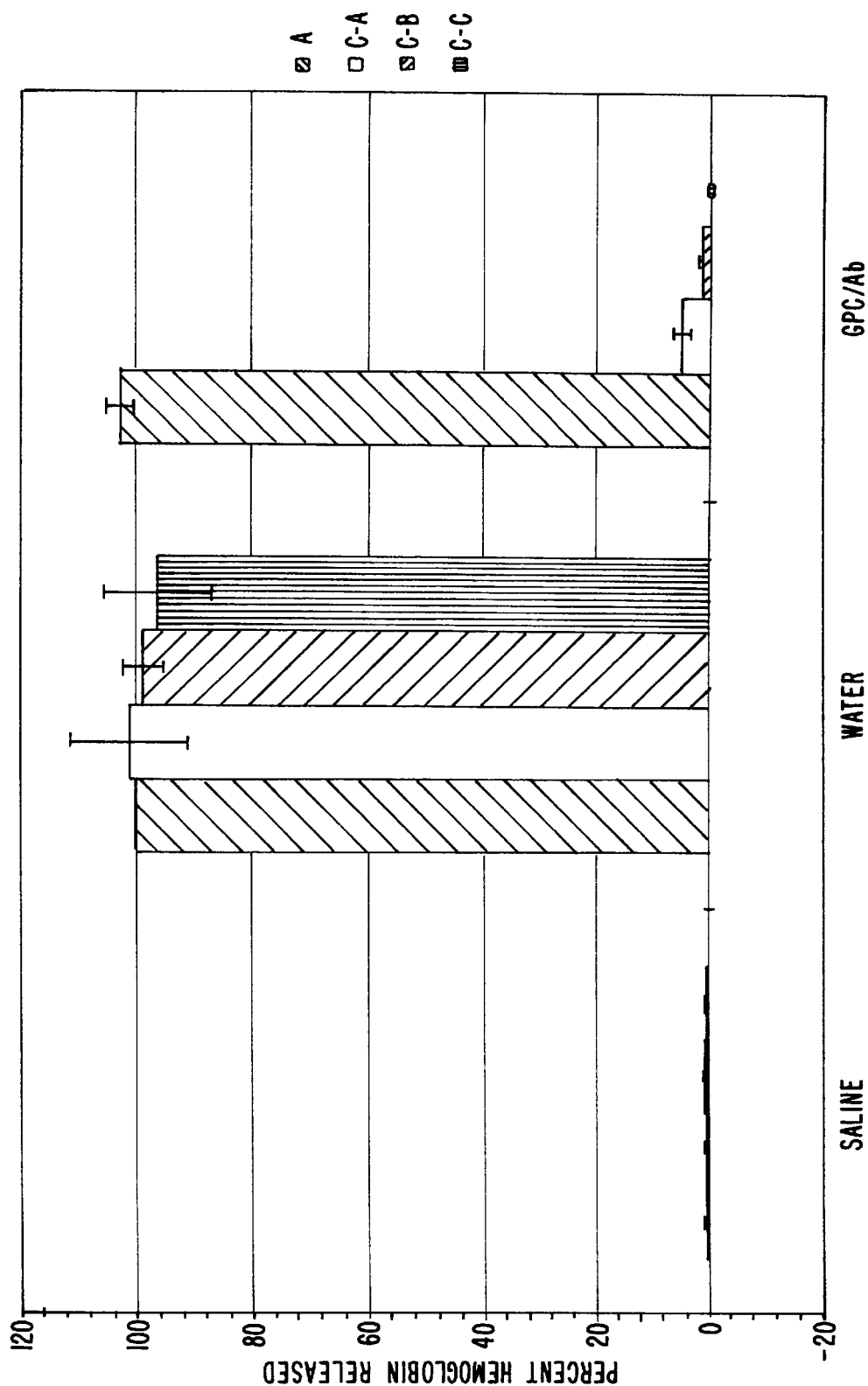
FIG. 2B shows a comparison of hemolysis rates, measured as a function of released hemoglobin, of alginate encapsulated red blood cells ("A"), and collagen coated alginate encapsulated red blood cells where the collagen nucleation reaction was carefully titrated using the three levels of added acetic acid shown in FIG. 1B ("C-A", "C-B", and "C-C") in saline, water and a solution including guinea pig complement plus antibody ("GPC/Ab").
Figure 3A:
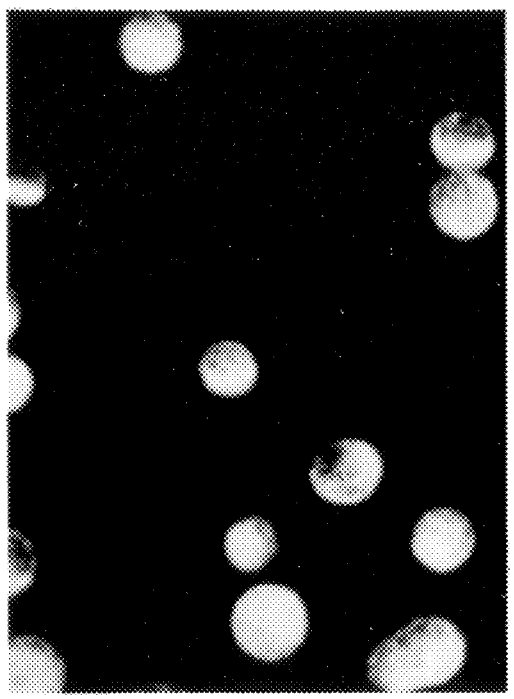
FIG. 3 shows photographs of red blood cells encapsulated in alginate and coated with collagen which was then crosslinked. The microcapsules were then treated with EDTA to dissolve the internal alginate capsule.
Figure 3B:
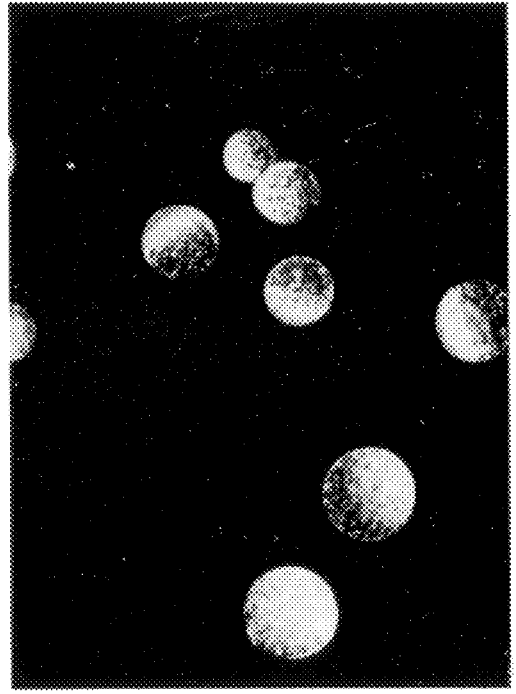
Figure 3C:
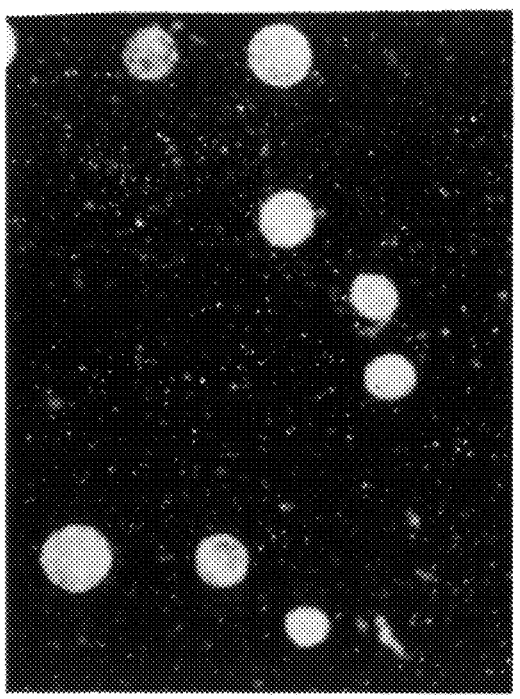
Figure 3D:
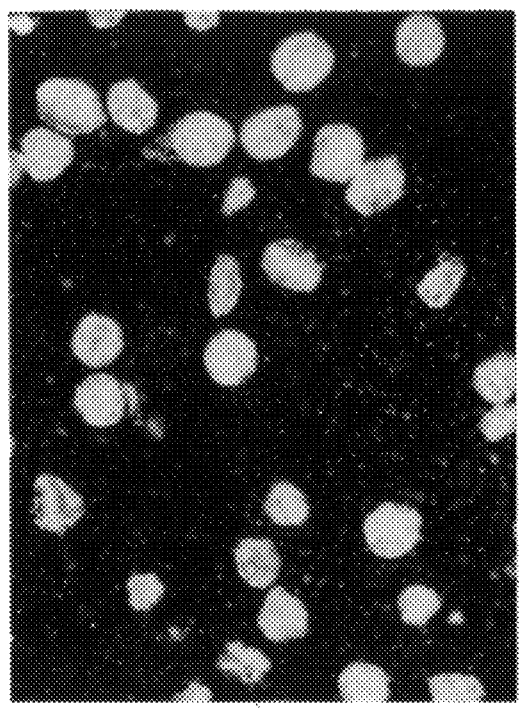

In a similar experiment, approximately 5,000 collagen coated, alginate encapsulated RBC beads were incubated either in saline, in water, or anti-sheep RBC antibody plus guinea pig complement. Aliquots (0.1 ml) were removed from each treatment after 4 hours, and diluted with four volumes of Drabkin's reagent for the spectrophotometric measurement of hemoglobin in the supernatant. Again, beads suspended in saline operated as a negative control, showing no hemolysis during the experiment, while suspension in water constituted a positive control showing nearly complete hemolysis, as shown in FIG. 2B. The figure illustrates the three collagen nucleation titrations described above and shown in FIG. 1B.

As shown in FIG. 2B, more precise titration of acetate according to the methods described above, allows the formation of a near complete immune barrier in collagen coated, alginate encapsulated beads.

Additional examples of collagen coating integrity are shown in FIG. 3. Collagen coated alginate encapsulated RBCs were treated with EDTA. The EDTA is intended to dissolve the Ca-alginate by chelating calcium. No RBCs are shown to be released from the microcapsules.

D. Viability Comparison of Single Coated and Collagen Cross-Linked Overcoated Canine Islets in Diabetic Balb/C Mice Single coated canine islets and collagen cross-linked, alginate overcoated canine islets were transplanted intraperitoneally into streptozocin-treated balb/c mice, and the results of these transplants are shown in Table 1. As shown in Table 1, the percentage of diabetic animals surviving greater than 30 days was larger for animals transplanted with collagen cross-linked alginate overcoated canine islets than for single-coated canine islets.

TABLE 1

| Graft | Graft IE | n | Graft Survival (days)* | >30 days success |
|---|---|---|---|---|
| Single Coated | 4000 | 8 | 8, 9 × 2, 10 × 2, 11, 12, 13 | 0% |
| Single Coated | 2000 | 13 | 2, 3, 4 × 2, 5, 6 × 3, 7 × 2, 8, 11, 19 | 0% |
| Overcoated | 4000 | 19 | 6, 9 × 2, 13, 14 × 2, 16, 17 × 2, 19, 20, 27, 30 × 2, 44, 48, 55 >93, >111 | 37% |

Single Coated: Islets single-coated with alginate.
Overcoated: Islets collagen cross-linked and overcoated with alginate.
* Primary non-function not included
IE: Islet Equivalents
>: Graft still ongoing While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A method of culturing viable cells, comprising coating said cells with at least one self-assembled layer of crosslinked mixed functionality polymer, and culturing said cells.

2. A method of culturing viable cells, comprising coating said cells with at least one self-assembled layer of crosslinked mixed functionality polymer, and culturing said cells, wherein said cells are first encapsulated wih a composition of alginate prior to coating said cells with said layer of crosslinked mixed functionality polymer.

3. A method of culturing viable cells, comprising coating said cells with at least one self-assembled layer of crosslinked collagen, and culturing said cells, wherein said cells are first encapsulated with a composition of alginate prior to coating said cells with said layer of crosslinked collagen.

* * * * *